United States Patent
Bloom et al.

(10) Patent No.: US 9,968,252 B2
(45) Date of Patent: May 15, 2018

(54) APPARATUS AND METHODS FOR DIAGNOSIS OF STRABISMUS

(71) Applicants: University Hospitals of Cleveland, Cleveland, OH (US); University Hospitals Medical Group, Inc., Cleveland, OH (US)

(72) Inventors: Jeffrey Bloom, Pepper Pike, OH (US); Kevin White, Boston, MA (US); Andreas Inmann, Cleveland, OH (US); Ryan Peters, Cleveland, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 0 days. days.

(21) Appl. No.: 14/432,834

(22) PCT Filed: Oct. 2, 2013

(86) PCT No.: PCT/US2013/062985
§ 371 (c)(1),
(2) Date: Apr. 1, 2015

(87) PCT Pub. No.: WO2014/055600
PCT Pub. Date: Apr. 10, 2014

(65) Prior Publication Data
US 2015/0265146 A1   Sep. 24, 2015

Related U.S. Application Data

(60) Provisional application No. 61/708,724, filed on Oct. 2, 2012.

(51) Int. Cl.
*A61B 3/10*   (2006.01)
*A61B 3/08*   (2006.01)
(Continued)

(52) U.S. Cl.
CPC ........... *A61B 3/085* (2013.01); *A61B 3/0008* (2013.01); *A61B 3/0025* (2013.01);
(Continued)

(58) Field of Classification Search
CPC ............. A61B 3/14; A61B 3/112; A61B 3/12
(Continued)

(56) References Cited

U.S. PATENT DOCUMENTS

| | | | | |
|---|---|---|---|---|
| 5,094,521 A | * | 3/1992 | Jolson | A61B 3/085 351/206 |
| 5,668,622 A | * | 9/1997 | Charbonnier | G06F 3/013 351/158 |

(Continued)

FOREIGN PATENT DOCUMENTS

GB            888376         1/1962

OTHER PUBLICATIONS

Ludtke et al., "Mathematical procedures in data recording and processing of pupillary fatigue waves", *Vision Research* 38 (1998) 2889-2896, Pergamon.

(Continued)

*Primary Examiner* — Hung Dang
(74) *Attorney, Agent, or Firm* — Richard M. Klein; Fay Sharpe LLP

(57) ABSTRACT

An apparatus for diagnosing and/or quantifying the degree of strabismus is disclosed. The apparatus includes a beam that supports at least two targets, a video camera, a light source for generating Purkinje reflexes, and a computer. The patient gazes at the targets while the video camera captures the patient's eyes. The frames of the video are then analyzed as described herein to determine the location of the pupil and the first Purkinje reflex. With this information, strabismus can be diagnosed, as well as the angle of deviation, which is (Continued)

useful for surgically correcting the strabismus. Methods of analyzing the frames are also discussed herein.

9 Claims, 13 Drawing Sheets

(51) Int. Cl.
 A61B 3/00 (2006.01)
 A61B 3/14 (2006.01)
(52) U.S. Cl.
 CPC .......... *A61B 3/0075* (2013.01); *A61B 3/0091* (2013.01); *A61B 3/145* (2013.01)
(58) Field of Classification Search
 USPC ........ 351/227, 237, 239, 240, 245, 222, 246
 See application file for complete search history.

(56) References Cited

U.S. PATENT DOCUMENTS

| 6,592,223 | B1* | 7/2003 | Stern | ...................... | A61B 3/028 |
| | | | | | 351/239 |
| 2009/0189974 | A1* | 7/2009 | Deering | .................. | G09G 3/02 |
| | | | | | 348/46 |

| 2012/0127426 | A1* | 5/2012 | Backus | .................. | A61H 5/005 |
| | | | | | 351/203 |

OTHER PUBLICATIONS

Hunter et al., "Vertical Location of the Corneal Light Reflex in Strabismus Photography", American Medical Association, 1998, Arch Ophthalmol, vol. 116, Jun. 1998, downloaded from http://archopht.jamanetwork.com on Dec. 16, 2013.
Hasebe et al., "Biometric Confirmation of the Hirschberg Ratio in Strabismic Children", *IOVS*, Dec. 1998, vol. 39, No. 13, pp. 2782-2785.
Braaf et al., "Calculating Angle Lambda ($\lambda$) Using Zernike Tilt Measurements in Specular Reflection Corneal Topography", J. Optom, vol. 2, No. 4, Oct.-Dec. 2009, pp. 207-214.
Barry et al., "Limbus Versus Pupil Center for Ocular Alignment Measurement with Corneal Reflexes", Investigative Ophthalmology & Visual Science, Nov. 1997, vol. 38, No. 12, pp. 2597-2607.
Barry et al., "Computational Principles in Purkinje I and IV Reflection Pattern Evaluation for the Assessment of Ocular Alignment", Investigative Ophthalmology & Visual Science, Dec. 1994, vol. 35, No. 13, pp. 4205-4218.
International Search Report and Written Opinion dated Jan. 8, 2014, PCT/US2013/062985, International Filing Date Oct. 2, 2013.

* cited by examiner

Right eye, Frame 1

Left eye, Frame 1

Right eye, Frame 1

Left eye, Frame 1

Right eye, Frame 7

Left eye, Frame 7

Right eye, Frame 7

Left eye, Frame 7

APPARATUS AND METHODS FOR DIAGNOSIS OF STRABISMUS

This application is a 371 of PCT Application No. PCT/US2013/062985, filed on Oct. 2, 2013, which claims priority to U.S. Provisional Patent Application Ser. No. 61/708,724, filed on Oct. 2, 2012. The entirety of each disclosure is hereby fully incorporated by reference.

BACKGROUND

The present disclosure relates to apparatuses or devices that can be used to determine whether a patient has strabismus and/or quantify the angle of strabismus for surgery or other corrective method that uses the angle of strabismus. Methods of using the apparatuses and methods of determining the angle of strabismus using data obtained from the apparatuses are also described herein.

Strabismus (commonly called "cross eyes" or "wall-eyed" or "squint") is a condition in which the eyes do not align in the same direction when focusing. Six different extraocular muscles surround the eyes and work together to focus both eyes on the same object. In a patient with strabismus, the muscles do not work together properly. When one eye focuses on a given object, the other eye is out of focus on the given object. When this occurs, two different images are sent to the brain, one from each eye (one in focus and one out of focus. This misalignment of the eyes prevents proper binocular vision and can reduce depth perception. In addition, because the brain cannot reconcile the mismatched images, the brain may learn to ignore the signal from the weaker eye, causing this eye to go blind.

Early diagnosis and correction or strabismus is the key to preventing blindness. Thus, strabismus should be detected in the first three years of a child's life. Unfortunately, while it is possible to diagnose strabismus in cooperative patients, diagnosing strabismus in non-cooperative patients is subjective and even experienced clinicians face inconsistent measurements. Up to 4% of children in the United States are affected by strabismus. The screening examinations used to diagnose strabismus are difficult with young children and infants, who are more likely to be non-cooperative due to difficulties in communication and comprehension.

The current standard in the diagnosis and treatment of strabismus of communicative adults is to perform the prism and alternate cover test (PACT). This method is effective, but requires the person performing the test to be a well trained and experienced examiner in order to be accurate. If the patient is a young child or uncommunicative, the standard is the Hirschberg test. In the Hirschberg test, the angle of deviation of the corneal light reflex within the pupil is determined.

One common treatment for strabismus is surgery to correct the muscles that control the movement of the eyes. Accurate diagnosis and measurement of the degree of deviation, i.e. the angle of strabismus, is helpful to ensure the success of the surgery and prevent the need for multiple procedures.

It would be desirable to provide apparatuses and/or methods that can permit strabismus to be determined for noncooperative patients and by lesser trained persons.

BRIEF DESCRIPTION

Disclosed in various embodiments herein are apparatuses and methods for determining the presence or absence of strabismus, and quantifying the degree of strabismus.

Briefly, the apparatus includes at least two targets, a zero target and a secondary target. A video camera and a light source for generating a Purkinje reflex are mounted upon (i.e. along an axis with) the zero target. The zero target and the secondary target are spaced apart to form a known angle relative to a fixed point where the patient/subject sits. The video camera records video of the patient fixating on each target. The video is sent to a computer, which examines each frame of the video. The pupil and the Purkinje reflex are identified. With information derived from their positions, the presence or absence of strabismus can be identified, and the angle of deviation can also be quantified. It should be noted that the phrases "angle of deviation" and "angle of strabismus" are used interchangeably herein. The Hirschberg ratio, i.e. the curvature of the cornea, can also be determined.

Disclosed herein are methods for determining and quantifying the degree of strabismus in a patient. A video camera and light source are used to capture a series of frames containing the patient's eyes. When the frames are being captured, the patient's head remains in a stationary position relative to the camera and the eyes gaze at a zero target and at least one additional target. The Purkinje reflex and the pupil of a given eye is then located by a series of steps. First, in each frame, the brightest points in the frame are identified to designate potential Purkinje points for a given eye in the frame. Next, clusters are defined based on the potential Purkinje points from all of the frames. The number of frames containing each potential Purkinje point is counted. Thus, a cluster is a combination of a potential Purkinje point and the number of frames containing that potential Purkinje point. The cluster (i.e. potential Purkinje point) with the highest number of frames is designated as being the Purkinje reflex for the given eye. Then, for each frame, based on the location of the Purkinje reflex for the given eye, a region of interest is identified in the frame for the given eye, and the pupil is searched for in only this region of interest (rather than the entire frame). For example, the pupil can be identified by locating potential pupil edges and then using a curve fitting algorithm to identify the pupil. The frames are subsequently sorted into at least four different groups corresponding to each eye and which target the eye was gazing. The angle of strabismus can then be calculated.

The Hirschberg Ratio and/or the angle of strabismus can be calculated using linear regression. It should be noted that only one central target (i.e. zero target) is needed to determine the angle of strabismus, if the literature value for the average Hirschberg Ratio is used. Alternatively, the Hirschberg ratio can be calculated for each eye.

Notably, the patient's head is not fixed in position relative to the video camera. Rather, the patient holds their head stationary, without the use of any external device. Some head motion is permissible and can be compensated for.

In particular embodiments, two additional targets are used, the two additional targets being a left target and a right target, for a total of three different targets (including the zero target). The left target and the right target are independently located at an angle of 15° to 45° to opposite sides of the zero target relative to the patient's head. In specific embodiments, the left target is located 30° to the left of the zero target relative to the patient's head. In other specific embodiments, the right target is located 30° to the right of the zero target relative to the patient's head. Additional targets can also be included if desired.

The brightest points in the frame can be identified by processing to remove noise, thresholding to locate possible bright points, and then applying a size filter and an eccentricity filter to identify the brightest points.

The pupil can be identified by applying an edge detection method and thresholding to detect possible edges, and then applying a size filter and an eccentricity filter to identify the potential pupil edges. Examples of various edge detection methods include the Sobel, Canny, Prewitt, and Roberts Cross methods. A curve fitting algorithm is then used to identify the pupil. Exemplary curve fitting algorithms include a circular or elliptical Hough transform.

The Hirschberg ratio for a given eye can be calculated by determining the displacement between the Purkinje reflex and the pupil at two different known angles. Generally, a known angle is identified for each group of the given eye (e.g. −30°, 0°, +30°). A displacement between a centroid of the Purkinje reflex and a centroid of the pupil for each group of the given eye is then calculated. The known angle versus the displacement can be plotted for the groups of the given eye. Linear regression is then used to determine the slope of a best-fit line for the plot, wherein the slope is the Hirschberg ratio for the given eye. The angle of strabismus can then be calculated by using linear regression to determine the y-intercept of the group corresponding to the zero target for the given eye.

Also disclosed in various embodiments herein is an apparatus for diagnosing strabismus in a patient, comprising at least two targets, a single video camera, a light source, and a computer. The two targets are a zero target and a secondary target, wherein the secondary target is located a first distance to one side of the zero target. The single video camera is mounted proximate the zero target. The light source is fixed in place relative to the video camera. The computer is used for analyzing data captured by the video camera.

In some specific embodiments described herein, the secondary target is a left target, and the apparatus further comprises a right target located a second distance to the other side of the zero target. The zero target, the left target, and the right target are present on a front surface of a beam, the first distance and the second distance being equal. The single video camera and the light source are mounted on a surface of the beam, usually the upper surface.

The zero target and the single video camera may be centered on a line perpendicular to a line connecting the zero target, the left target, and the right target. The light source may also be in line with the zero target and the single video camera.

The zero target, the left target, and the right target may each include a first light and a second light, the two lights being of different colors. The first light and the second light of each target may be located behind a transparent plate having a picture in the form of a human-shaped face, or other pictures/shapes as desired.

In some embodiments, the beam can be rotated between a horizontal position and a vertical position, and can be fixed in any desired location between these two positions. In other embodiments, the beam is mounted upon a stand. The stand can be mobile and/or adjustable in height.

In particular embodiments, the left target is located 30° to the left of the zero target relative to a fixed point about 1 meter in front of the zero target. In others, the right target is located 30° to the right of the zero target relative to a fixed point about 1 meter in front of the zero target.

The apparatus may have two speakers, one speaker being located on either side of the zero target. A speaker could be located behind the zero target if desired.

In other embodiments of the apparatus described herein, the zero target, the single video camera, and the light source are contained in a first physical module. The secondary target is contained in a second physical module.

The first physical module and the second physical module may each comprise a single speaker.

Two different means of presenting the two modules are contemplated. In some embodiments, the first physical module and the second physical module are mounted onto a common transverse beam. In others, the first physical module is mounted on a vertical stand, the second physical module is mounted on a transverse beam extending from the vertical stand, and the transverse beam can be rotated around the vertical stand. In others, the first physical module and the second physical module are mounted on two separate stands. The stands may be independently adjustable in height.

In yet another set of variations of the apparatus described herein, the zero target and the secondary target are mounted on a flexible surface. The single video camera and the light source are contained in a physical module. The physical module and the flexible surface can be mounted on, for example, a wall. In other embodiments, the physical module is mounted on a vertical stand which is adjustable in height. The flexible surface is supported by a crossbar extending transversely from the vertical stand.

In some variations, the secondary target is a left target, and the apparatus further comprises a right target located a second distance to the other side of the zero target on the flexible surface.

In all of the different apparatuses described herein, the light source may emit infrared light and the video camera is able to capture infrared radiation. The apparatus may further comprise a metering system for measuring the distance from the video camera to the head of an associated patient.

The apparatus does not include any equipment for fixing the head of an associated patient in place relative to the video camera.

In particular embodiments, the single video camera is a monochrome camera.

In other embodiments, the zero target is different from the secondary target. For example, the targets may have different numbers of lights, or different colors, or a different transparent face arrangement.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
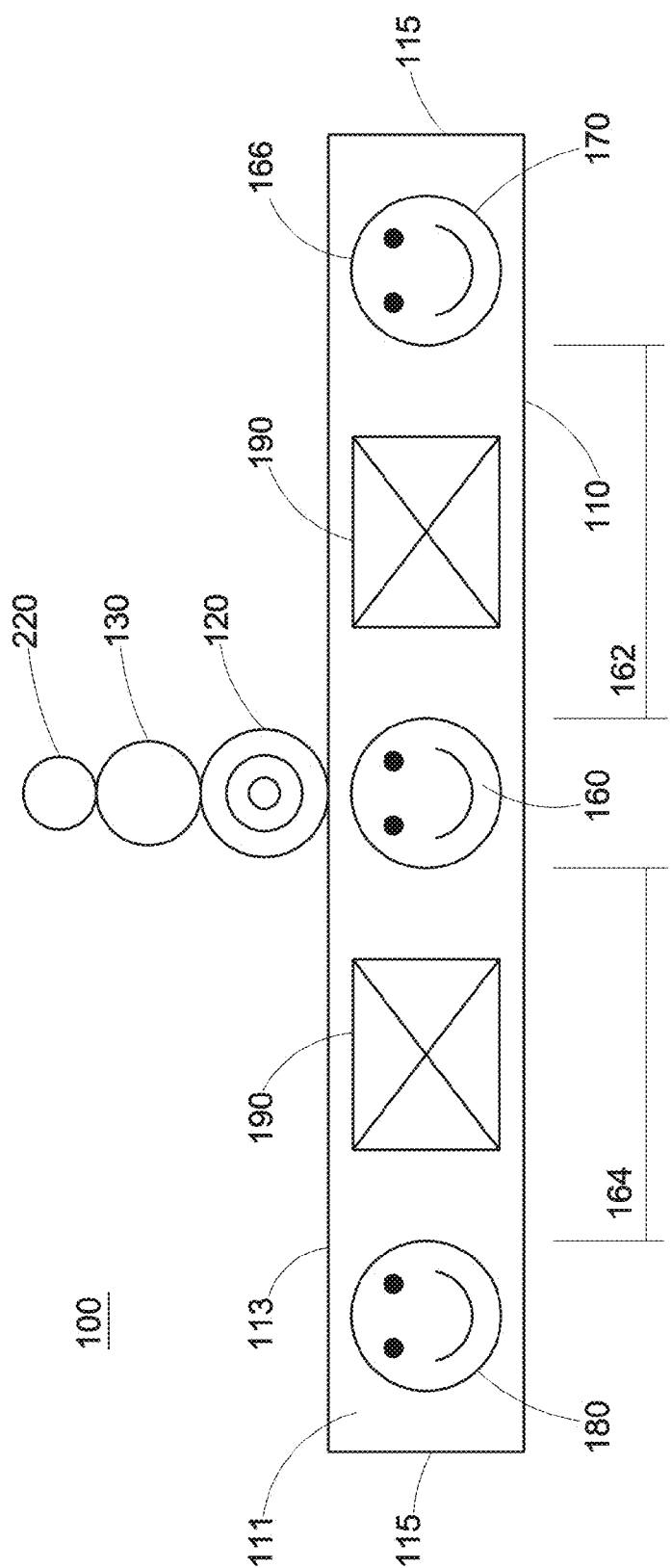
FIG. 1 is a front view of one exemplary embodiment of an apparatus for diagnosing strabismus of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The present disclosure relates to an apparatus that can be used to determine the presence or absence of strabismus, and for quantifying the angle of deviation (which is useful for corrective surgery). In addition, the apparatus can be used both for strabismus screening and as a quantitative tool for surgery planning. The ability to quantify the results accurately streamlines the diagnostic process and decreases the number of corrective surgeries needed, lowering the total medical costs for patients and their families. The apparatus is used to capture several frames of the patient's eyes as the patient looks at different targets. Computer processing techniques can be used to analyze the frames and determine whether strabismus is present and if so its severity. It is believed that the present apparatus is able to diagnose esotropias, exotropias, hypertropias, and hypotropias.

Figure 2:
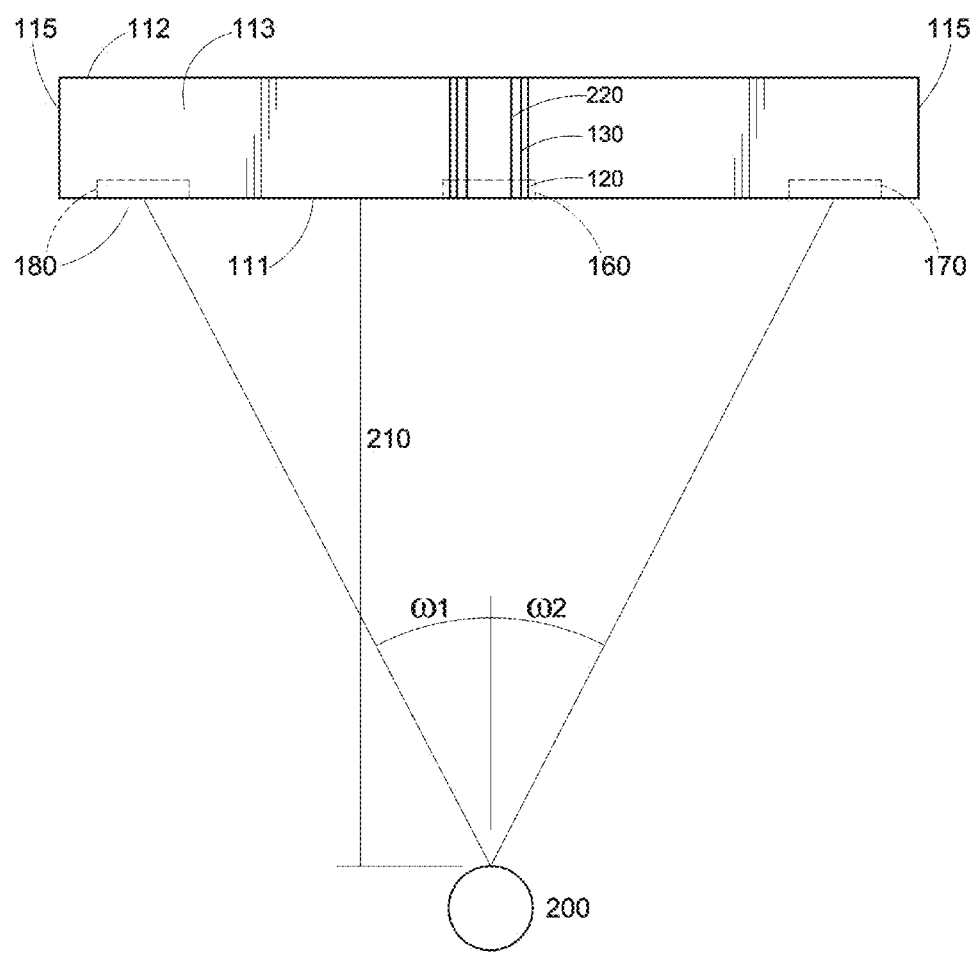
FIG. 2 is a top view of the apparatus of FIG. 1.
Figure 3:
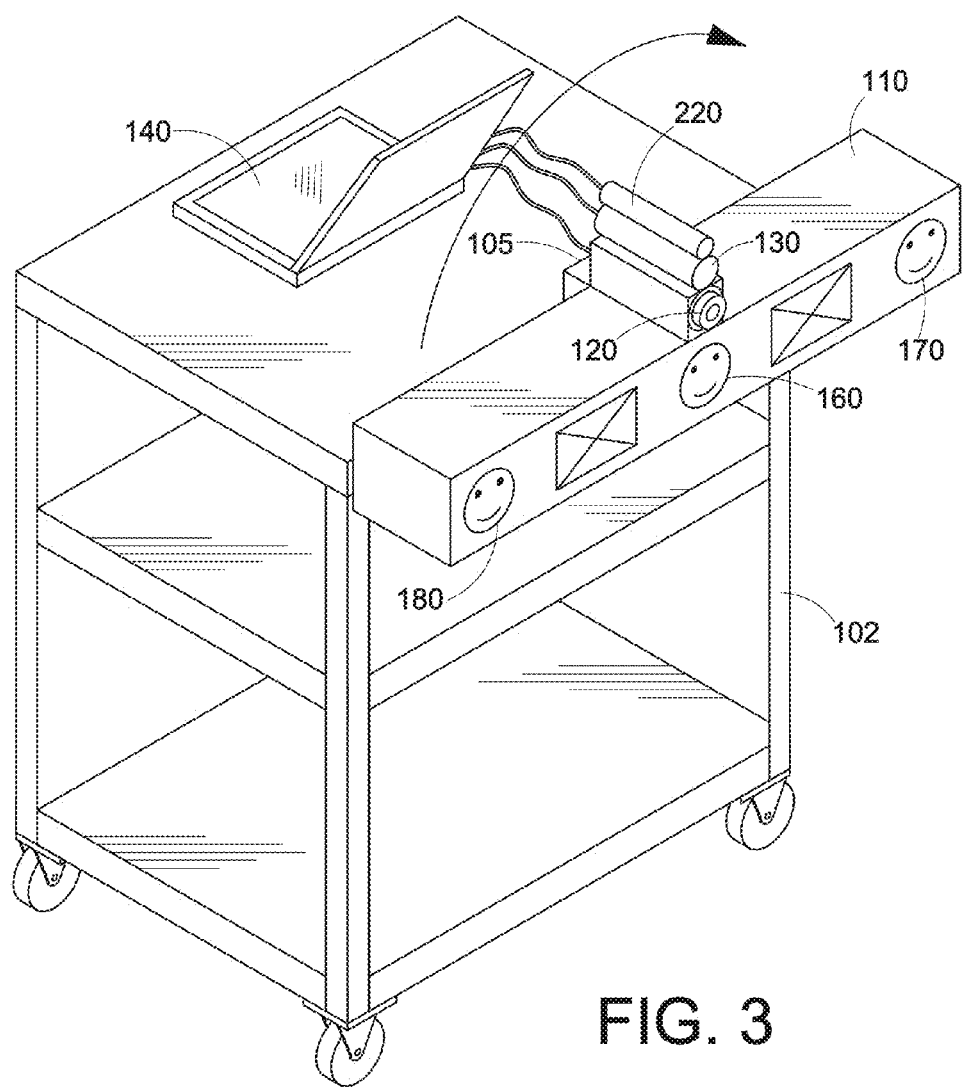
FIG. 3 is a perspective view of the apparatus of FIG. 1 mounted upon a mobile surface.

An exemplary embodiment of the apparatus is shown in FIG. 1 and FIG. 2. FIG. 1 is a front view, and FIG. 2 is a top view. FIG. 3 is a perspective view of the apparatus mounted upon a mobile stand.

The apparatus 100 includes a beam 110, a single video camera 120, and a light source 130. A computer 140 is connected to the camera and the light source (visible in FIG. 3). The beam itself has six rectangular surfaces, and may be described as having a rectangular solid shape. The beam 100 includes a front surface 111, a rear surface 112, an upper surface 113, a lower surface 114, and two side surfaces 115. The beam 110 is mounted to a stand 102 which elevates the beam to the desired height. The stand 102 can be adjustable in height. In some embodiments, the stand may be mobile. For example, the stand may be a cart with wheels as depicted in FIG. 3. The beam 110 can also be mounted to the stand 102 such that the beam can be rotated between a horizontal position and a vertical position, for example using a pivot 105 in the center of the rear surface 112 of the beam (indicated by an arrow with a 90° arc). Of course, it is contemplated that the beam can be fixed in any particular position between the horizontal position and the vertical position, and that the beam can be rotated either counter-clockwise or clockwise. The front surface 111 of the beam remains pointing forward of the stand 102 in any of these positions.

Present along the front surface 111 of the beam are a zero target 160, a left target 170, and a right target 180. The zero target 160 is located between the left target 170 and the right target 180, and may also be considered a center target. The left target 170 is located a first distance 162 to one side of the zero target. The right target 180 is also located a second distance 164 on the other side of the zero target. Usually, the first distance and the second distance are equal. Two speakers 190 are also located on either side of the zero target. Each speaker is located between two of the targets, and can be located proximal to the left target and the right target. In more particular embodiments, the speakers are at least three times further from the zero target than they are from the left target or right target. The speakers are usually used to provide an aural cue to the patient. The speakers are optional, though useful in fixing the gaze of the patient. It is also contemplated that a speaker can be placed behind the zero target.

Referring to FIG. 2, the three targets 160, 170, 180 are spaced apart so that at a fixed point 200 located a given distance 210 away from the beam 110, a significant angle ω1, ω2 is formed between two adjacent targets. The patient is seated at this fixed point 200 when the apparatus is being used. As depicted here, the left target 170 is located 30° to the left of the zero target 160 relative to the fixed point 200, which is about one (1) meter in front of the zero target and perpendicular to the beam. The right target 180 is also located 30° to the right of the zero target relative to the fixed point 200. At this distance, this results in the left target and the right target being spaced about 57 centimeters (cm) away from the zero target. It should be noted that the two angles ω1, ω2 can be different from each other, though they are usually the same for convenience. The angles ω1, ω2 can also be of any value, though they are usually between 15° and 45°.

In some embodiments, each target 160, 170, 180 includes a first light and the second light, the two lights being of different colors. The lights are usually light emitting diodes (LEDs). In embodiments, one light is red, and one light is white. The lights are located behind a transparent plate. In some embodiments, the plate may include a picture in the form of a human shaped face 166 that has two dots and an arc (i.e. two eyes and a smile). The targets 160, 170, 180 and the speakers 190 are used to visually attract the attention of the patient, fixating his gaze on a given target so that the video camera can be used to capture the patient's eyes. In these embodiments, the three targets are configured in the same way. It is contemplated that the plates are switchable to have different pictures to adapt to the patient's preference. Generally, the plates/pictures can be of any shape that can obtain the visual attention of the patient.

In some alternate embodiments, two different kinds of targets are used in the apparatus. For example, the zero target may contain two lights of different colors, while the left target and the right target contain three lights of different colors. This permits the use of additional attractive patterns for fixating the patient's gaze.

The video camera 120 is mounted proximate the zero target 160, or in other words at the center of the beam, so that the video camera can focus on the patient's eyes when the patient's head is facing the zero target. The video camera 120 and the zero target 160 should be centered on a line that is perpendicular to a line connecting the three targets 160, 170, 180. For example, the video camera can be above, below, or behind the zero target. The video camera is used to capture uncompressed video that is streamed in real-time to the computer. In embodiments, the video camera is a monochrome camera. The video camera may have a high resolution, such as 1920×1080 pixels, or 1280×1024 pixels, or even higher. The video camera may run at a rate between 10 to 100 frames per second, with an appropriate balance between frame rate and computation time so as to obtain a reasonable number of frames that can be processed within a short period of time. The apparatus includes a single video camera, i.e. only one video camera, unlike other systems that use two cameras.

The light source 130 is mounted in line with the video camera 120 and the zero target 160, and is used to provide a known reflection off of the eye (i.e. Purkinje reflex). The light source is generally of any wavelength which can be captured by the video camera. The light source 130 is fixed in place relative to the video camera 120, so that the Purkinje reflex is in a known location in the resulting frames captured by the video camera. In embodiments, the light source emits infrared or near infrared light. For purposes of this disclosure, the term "infrared" refers to wavelengths of 750 nm to 1 mm, and the term "near-infrared" refers to wavelengths of 750 nm to 1400 nm. In particular embodiments, the light source 130 emits infrared light and the video camera 120 is able to capture infrared radiation. However, the use of visible light is also contemplated. It should be noted that the light source is not a perfect point source.

The apparatus 100 is intended to be placed so that the zero target is one (1) meter in front of the patient, and the left target and the right target are on either side of the patient's head at an equal distance. Notably, the patient's head is not fixed in place relative to the video camera. Unlike prior devices that use a head restraint, chin rest, bite bar, or other fixation device to maintain the patient's head in a known location relative to the camera, the present apparatus allows the patient to move their head freely about. This provides an additional level of comfort for the patient, which helps maintain the patient's cooperation, as well as being easier for the operator. The patient's head remains in a stationary position relative to the camera, and small movements of the head can be tracked and compensated for by the apparatus.

In some embodiments, a metering system 220 is included for measuring the distance from the video camera 120 to the head of the patient (i.e. point 200). This information can be useful during computer processing to determine the location of the patient's eyes and pupils. An exemplary metering system may include one or more lasers which are directed at the patient's head (usually the forehead and possibly other points, not near the patient's eyes). In such embodiments, the lasers of the metering system are of a different wavelength from that used by the light source 130 and the video camera 120, so that the metering system does not cause errors in the computer analysis and/or can be filtered out. Another metering system may use ultrasound to determine the distance between the video camera and the patient's head. The metering system 220, when present, is mounted proximate to the video camera 120, and is depicted here as being above the light source 130. Alternatively, the camera may be a fixed focus camera. The distance from the video camera to the patient's head can be estimated using methods known in the art.

In this regard, the video camera and the metering system can be used to compensate for head movement. The video camera can be used to measure side-to-side movement of the patient's head. The metering system can be used to measure the towards-away motion of the patient's head relative to the camera. The combination of both measurements can be used to compensate for head movement during measurement by using a computer algorithm. Generally, because the video camera and the light source are stationary, if the head is stationary the location of the Purkinje reflex should also be stationary when the patient is gazing at a given target. The location of the Purkinje reflex can be tracked between frames. If the Purkinje reflex does move, this indicates that the patient's head has moved, and the angle that the patient is actually looking can be determined by the new location of the Purkinje reflex. The use of the metering system permits the distance between the camera and the patient to be actually measured instead of assumed as being constant. As a result, it is possible that some of the frames actually capture the patient looking at a determined angle of, for example, +28° instead of at the 30° target. This difference can still be taken into account when calculating the Hirschberg ratio.

The apparatus for diagnosing strabismus also includes a computer 140 that is used to analyze the data captured by the video camera 120. The computer can receive data from the video camera via a physical connection or a wireless connection.

The video data to be processed by the camera is usually captured over a period of 10 seconds to 15 seconds. Initially, the operator of the apparatus enters the patient information and makes various selections for the recording procedure (when video is captured). The patient is seated one meter away from the beam, perpendicular to the zero target. The measurement should take place in a dark room, which increases the contrast in the resulting video between the reflections (i.e. Purkinje reflexes) and the face of the patient. The patient is asked to hold their head still, and to move only their eyes at the designated target.

At beginning of the video capture portion of the procedure, the three targets are initially dark. The recording sequence begins when one target is lit, attracting the patient's attention to that target. If desired, a sound can also be played near the target to cue the patient or to attract the patient's attention. The white LED flashes, and then the white LED is extinguished and the red LED flashes. The light from the light source 130 reflects off of the patient's cornea, creating a first Purkinje reflex which is visible to and captured by the video camera 120. The red LED of the target is then extinguished. Next, a second target is lit, and the patient's eyes move towards that target. Finally, the third target is lit, and the patient's eyes move towards that target. The video camera continuously captures video of the patient's eyes. If the video camera is recording at a rate of 15 frames per second, then over the capture period a total of from about 150 to about 225 frames are captured that contain both eyes of the patient.

Next, the computer is used to run specialized software that analyzes the video frames to determine whether strabismus is present. In this regard, the software locates the first Purkinje reflex and the pupil of each eye. The first Purkinje reflex (i.e. the first Purkinje image) is the reflection of the light source from the outer surface of the cornea. The centroids of the first Purkinje reflex and the pupil are then identified. The distance between the centroids of the first Purkinje reflex and the pupil is measured for both eyes in each frame. If no strabismus is present, the two distances for each eye should be the same. If strabismus is present, the distances for each eye will differ, and the degree of difference can be used to quantify the degree of strabismus. The Hirschberg ratio, which is the linear movement of the first Purkinje reflex per angular unit of eye rotation, can then be determined. The software can use this calculated Hirschberg ratio to quantify the angle of deviation, which is the horizontal angle of eye misalignment. The values used to determine the Hirschberg ratio and the angle of deviation are based on averages from all of the video frames. This statistical approach improves the resulting values.

It should be noted for clarity that the first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens.

It should be noted that references to the pupil may refer either to the entire pupil, the edge/boundary of the pupil, or to the centroid of the pupil, as dictated by the context. Similarly, references to the first Purkinje reflex may refer either to the entire reflection, the edge of the reflection, or to the centroid of the reflection, again as dictated by the context.

Two principles are used in determining whether strabismus exists. The first principle is that as the eyes move to different targets, the pupils will move but the first Purkinje reflex generally will not move. The location of the first Purkinje reflex, along with some geometric relationships, can be used to track the position of the head. The second principle is that the distance between the Purkinje reflexes in each eye is always the same.

The computer analysis is performed in several steps. First, each frame is individually analyzed to identify and locate potential Purkinje reflexes in the frame. Second, all of the frames are combined, and the potential Purkinje reflexes form clusters that determine the correct Purkinje reflex. Third, based on the location of the Purkinje reflex, a region of interest is identified in each frame in which the pupil should be located. The edge of the pupil is identified in the region of interest. Fourth, using this information, the Hirschberg ratio can be determined for each eye. Fifth, the angle of deviation is to be determined for each eye. These processing steps are described in further detail below.

In analyzing the frames, the software eventually divides the captured frames into six different groups, based on the two eyes and three target locations (the number of groups will vary with the number of target locations). These six different groups are used to determine the Hirschberg ratio of each eye and any angle of deviation in the eye. The frames can be preliminarily sorted or identified into the six different groups prior to the computer analysis, if desired, because the analysis is performed individually around each eye regardless of which group the frame belongs to. For example, the frames can be divided into their group based on information available to the software. For example, the computer software knows in which order the targets were illuminated, which provides information on which target location a given frame refers to and thus which group the given frame should be placed into. In each frame, the computer is also able to determine relatively easily which eye is the left eye and which eye is the right eye. Additional processing may also provide further information that facilitates the sorting into the six or more different groups. For example as explained further herein, the frames are processed to identify the pupil and the Purkinje reflex. The relative location of the pupil to the Purkinje reflex can also be used to determine which target location is being viewed in that particular frame. For example, if the Purkinje reflex is to the left of the pupil, it is likely the patient was looking at the right target rather than the left target. Generally, however, the frames are sorted after analysis so that erroneous frames can be discarded if the patient is not looking at the target.

The following discussion assumes that 200 frames were captured by the video camera and are being analyzed together. The video camera captured a session in which the three targets were located at −30°, 0°, and +30° (negative indicating to the left). In this discussion, it is also assumed that each frame is being analyzed as a whole, i.e. with both eyes being present in the frame. As noted further herein, the frame can be divided into two cells, one cell containing the left eye and one cell containing the right eye. The cells containing the left eye can be considered to form a left eye set, and the cells with the right eye can be considered to form a right eye set. The computer analysis discussed herein could be done on the cells containing only one eye.

It should be noted that the total frame (both eyes) can have a resolution of 1920×1080 pixels, or higher. Assuming that the average human head has a width of 18 cm, and that the frame captures a total width of twice the human head (i.e. 36 cm in width), the theoretical pixel resolution of the frame would be approximately 0.19 mm/pixel, or 5 pixels/mm. The average human pupil has a diameter of between 3 mm and 9 mm, or in other words would take up between 15 pixels and 47 pixels. Thus, the entirety of both pupils should be detectable in the frames captured by the video camera. If the camera is fixed so that the frame is focused on a narrow width that captures only the eyes (e.g. a 15-cm width instead of 36-cm width), then the pixel resolution would be even greater. The Purkinje reflex should also be detectable as taking up multiple pixels. In addition, it should be noted that the original frame is grayscale. It should be noted that while the pupil is referred to herein, the analysis identifies the pupil by locating the boundary (i.e. the edge) of the pupil.

In the first step of analysis, potential Purkinje points are identified in each frame. The frame is first processed to remove noise and to smooth out the image. This can be done using a Gaussian filter or a Laplace filter, as desired. Dynamic or adaptive thresholding is then used to identify the brightest points in the frame. In this regard, the first Purkinje reflex is the reflection of the light source on the cornea, and the two Purkinje reflexes (one in each eye) should be among the brightest objects in the frame. Binning can be used to adjust the levels of the threshold for each particular frame (where the grayscale image is converted into a binary image), where each pixel is placed in a bin according to its magnitude, so that the pixels with the brightest points can be identified. The thresholding can be automatically adjusted to include/exclude certain bins from consideration. The pixel locations of these bright points are recorded. Each impulse point is passed through a size filter to determine whether the particular bright point has the correct size, and through an eccentricity filter to determine whether it has the correct shape (i.e. circular). The bright points which successfully pass the size and eccentricity filters can then be recorded as the potential Purkinje points for this frame. Any desired number of potential Purkinje points may be recorded for a given frame, though this number should generally be limited, for example to a maximum of five potential Purkinje points. It should be noted that in this first step, it is possible that incorrect locations are identified for the true Purkinje reflex. The pixel locations of the potential Purkinje points are recorded. It should be noted that these pixel locations usually refer to groups of pixels. For example, 16 adjacent pixels of equal brightness are recorded as a potential Purkinje point. Also, the pixel locations can be recorded in any form. For example, the 16 adjacent pixels can be recorded by their individual pixels, or by recording the four corners of the square that define the 16 pixels, or as the center and radius of a circle that surround the 16 pixels.

In the second step of analysis, the 200 frames are statistically analyzed together to determine the correct Purkinje reflex for the given eye. All of the potential Purkinje points from the frames are combined. A cluster is defined at each location (i.e. the coordinates) of a potential Purkinje point, and the number of frames containing a potential Purkinje point at that location (i.e. at the same coordinates) is counted. In other words, a given cluster contains the coordinates of a potential Purkinje point and the number of frames containing that potential Purkinje point. The two clusters with the highest number of frames are considered to be the correct Purkinje reflexes, one for each eye. This conclusion can be verified; for example, the two Purkinje reflexes should be a minimum distance apart and should be a fixed distance apart (see the second principle above). This statistical approach of determining the correct Purkinje reflex separates good data points from the outliers.

Any frames which did not contain either of the correct Purkinje reflexes may be considered to be an outlier and can be discarded from further analysis. This could happen, for example, if the frame was taken when the eye was in motion from the zero target to the target 30° away, and the eye was at only a 10° angle.

In the third step of analysis, the pupil is identified in each eye. As noted above, the first Purkinje reflex is the reflection of light off the cornea. Because the cornea covers the pupil, the first Purkinje reflex is necessarily located near the pupil. As a result, a region of interest (ROI) can be designated around the Purkinje reflex in the cell. Subsequent computer analysis is performed only on the pixels within this region of interest. By eliminating the rest of the cell, computer processing is reduced and the speed of the analysis can be increased. Given that the pupil may have a width of 47 pixels (as explained above), an appropriate size for the region of interest can be, for example, 100×100 pixels, to ensure that the entire pupil is within the region of interest. For example, if the centroid of the first Purkinje reflex is determined to be at pixel location (500,500), then the region of interest would be the square denoted by connecting the four pixels (450, 550); (550, 550); (450, 450); and (550, 450). The size of the region of interest can be modified as appropriate. For example, at a higher pixel resolution, the region of interest may be 200×200 pixels. The region of interest can be shifted if necessary to remain within the frame. For example, if the centroid of the first Purkinje reflex is determined to be close to an edge of the frame, then the region of interest can be shifted so that the centroid is not at the center of the region of interest.

At this point in the analysis, two regions of interest have been identified in each frame, corresponding to the two eyes in the frame. Each frame can now be divided into two cells, one cell corresponding to the region of interest containing the left eye and the other cell corresponding to the region of interest containing the right eye. The cells containing the left eye can be considered to form a left eye set, and the cells with the right eye can be considered to form a right eye set.

Potential pupil edges can be identified in the region of interest (i.e. the cell) using edge detection algorithms known in the art, such as the Sobel, Canny, Prewitt, or Roberts Cross methods. Thresholding can also be used to determine pixels that are likely to be an edge of the pupil. The potential pupil edges are then passed through a size filter to determine whether they have the correct size, and through an eccentricity filter to determine whether they have the correct shape. The pupil edges which successfully pass the size and eccentricity filters are then recorded as the potential pupil edges for the cell. For example, the Hough transform can be used to detect whether the potential pupil edges are circular. The pixel locations of the potential pupil edges are recorded. The identified pupil edges can then be transformed into a circle or ellipse that identifies the boundary of the pupil, and from which a centroid of the pupil can be calculated. For example, a curve fitting algorithm can be used. This results in the boundary of the pupil being located for each eye in each frame.

An illustration of the computer analysis is shown in FIGS. 4-11. FIGS. 4-7 are the two regions of interest from frame number one of approximately 200 frames captured in a session. FIGS. 8-11 are the two regions of interest from frame number seven of the same session. It should be noted that the original frames had a resolution of 1280×1024 pixels, but the regions of interest are only 100×100 pixels. Focusing on the regions of interest decreases computer processing significantly when identifying the pupils.

Figure 4:
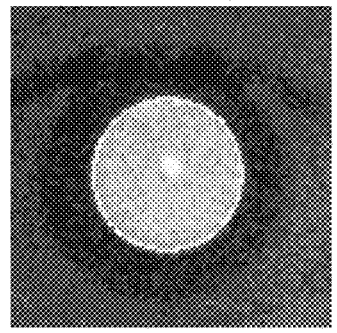
FIG. 4 shows a region of interest of the right eye illustrating the location of the Purkinje reflex in a first frame from a video capture session. A circular bold white line is also present to show the identified location of the pupil.
Figure 5:
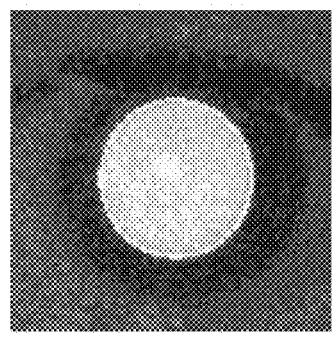
FIG. 5 shows a region of interest of the left eye illustrating the location of the Purkinje reflex in the first frame from the video capture session of FIG. 4. A circular bold white line is also present to show the identified location of the pupil.
Figure 8:
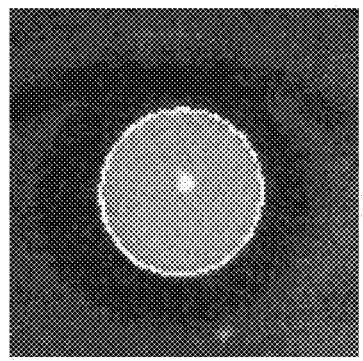
FIG. 8 shows a region of interest of the right eye illustrating the location of the Purkinje reflex in a seventh frame from the same video capture session of FIG. 4. A circular bold white line is also present to show the identified location of the pupil.
Figure 9:
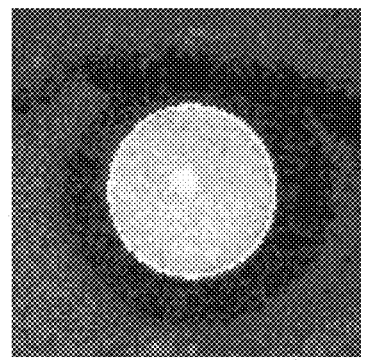
FIG. 9 shows a region of interest of the left eye illustrating the location of the Purkinje reflex in the seventh frame from the video capture session of FIG. 4. A circular bold white line is also present to show the identified location of the pupil.

FIG. 4 is the right eye, and FIG. 5 is the left eye, both from frame number one. FIG. 8 is the right eye, and FIG. 9 is the left eye, both from frame number seven. These figures are provided to show how the Purkinje reflex is located. However, it should be noted that the analysis for locating the Purkinje reflex is performed on the frame, not only the region of interest shown here.

In these figures, the pupil edge is shown in white, and the relative impulse strength of the pixels within the pupil edge is shown. Looking at FIG. 4 and FIG. 8, it is easy to identify the Purkinje reflex near the center of the pupil of the right eye. However, it is not as easy to identify the Purkinje reflex in the left eye in FIG. 5. Here, there are several bright pixels. If FIG. 5 were considered alone, it might be difficult to determine where the Purkinje reflex is located. However, in FIG. 9, the Purkinje reflex is easier to identify. This illustrates the principle that the statistical analysis of a large number of frames is likely to identify the correct Purkinje reflex.

Figure 6:
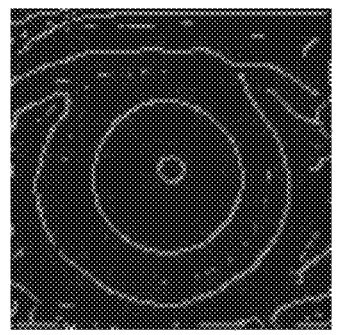
FIG. 6 shows the edges detected during processing to identify the pupil in the right eye of the first frame of FIG. 4.
Figure 7:
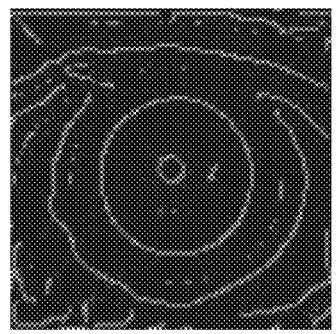
FIG. 7 shows the edges detected during processing to identify the pupil in the left eye of the first frame of FIG. 5.
Figure 10:
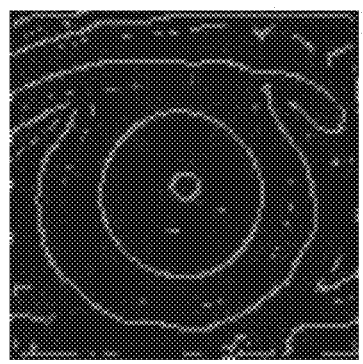
FIG. 10 shows the edges detected during processing to identify the pupil in the right eye of the seventh frame of FIG. 8.
Figure 11:
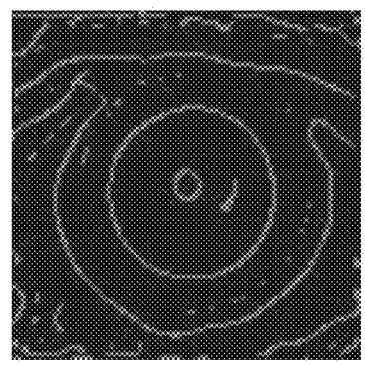
FIG. 11 shows the edges detected during processing to identify the pupil in the left eye of the seventh frame of FIG. 9.

Next, FIG. 6 is the right eye, and FIG. 7 is the left eye, both from frame number one. FIG. 10 is the right eye, and FIG. 11 is the left eye, both from frame number seven. These figures are provided to show how the pupil edge is located. In these figures, the line edges are identified by edge detection are shown. Referring now to FIG. 6, and comparing with FIG. 4, the ridge of the eye is seen as a parabolic arc near the top of the figure. The circle denoting the Purkinje reflex is not considered as a potential pupil edge because it was previously determined to be the location of the Purkinje reflex. The larger partial circle under the ridge is the iris, which surrounds the pupil and the edge of the Purkinje reflex. The circle outside the Purkinje reflex can be identified as the pupil. The partial circle of the iris is not identified as the pupil because if given the choice between this partial circle and the circle which is the actual pupil, the iris is always larger than the pupil. It can be seen that the pupil in FIG. 10 is also in approximately the same location as that of FIG. 6.

Next, the Hirschberg ratio (HR) and the angle of deviation can be calculated. If the frames were not already sorted into at least six different groups (based on the two eyes and the three target locations), then they are now sorted into the different groups. The Hirschberg ratio for each eye can be calculated using the different groups for that eye. It is noted that each eye has at least three different groups (zero, left, right) that have a known angle (i.e. 0°, −30°, +30°). Additional groups may be present due to compensations made for head movement as previously described. For example, there may be a group at an angle of +28°. The displacement between the Purkinje reflex and the pupil center can be determined based on the locations of the groups. The various pairs of angle vs. displacement (one for each group) can be graphed. Linear regression (y=mx+b) provides the slope, which has the units of degrees per millimeter, i.e. the Hirschberg ratio, and can be converted to prism diopters/mm (PD/mm) as desired. If the two HR values are close to each other and are both within the value and standard deviation expected from literature, then the two HR values are averaged and outputted by the software as the HR. If one of the HR values is outside the range, then it is ignored as the outlier and the "good" HR value is reported by the software.

Knowing the slope m, the angle of strabismus, i.e. the angle of deviation (AOD), can be calculated using the zero group and determining its y-intercept b. The AOD can be used by surgeons to correct strabismus. The standard deviations for the Hirschberg ratio and the angle of deviation can also be calculated and provided, if desired.

Note that if desired, the HR value does not need to be calculated as described above. Rather, the literature value for the HR (21 PD/mm) can be used instead, and the angle of strabismus calculated by using the zero group. In such an embodiment, the HR would not be reported.

Besides the full quantitative testing mode described above, which measures the actual Hirschberg ratio and provides the angle of deviation, it is also contemplated that a second functionality could be provided with the apparatus. In a screening mode, only a qualitative determination of whether the patient has strabismus would be provided. In this mode, rather than calculating the actual Hirschberg ratio, the Hirschberg ratio would be assumed to be the average literature value of 21 PD/mm. The analysis would not use all three targets, but only the zero (center) target. The resulting output would be a statement indicating whether the patient has strabismus.

Figure 12:
FIG. 12 is a screenshot of the initial page of the user interface.

The user interface for the apparatus for diagnosing strabismus is clean and simple to use, controls the entire apparatus, and streamlines the procedure to maximize efficiency. FIGS. 12-15 are several views of the interface at different steps of the strabismus diagnosis procedure. In FIG. 12, the patient ID and the operator are identified. The patient information can be entered and stored, and the resulting patient output can also be saved and printed for storage or for medical records.

Figure 13:
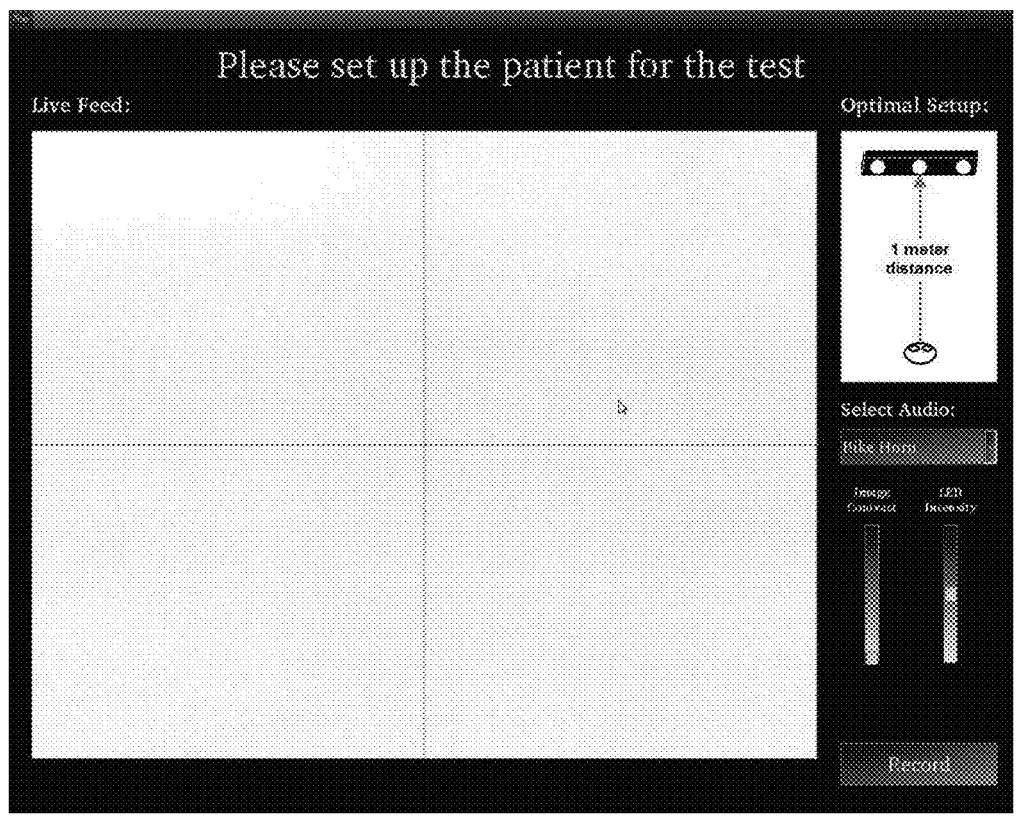
FIG. 13 is a screenshot of the user interface explaining the positioning of the patient and setting up of the light/sound options for the video capture session.

FIG. 13 shows the user interface explaining how to position the patient correctly before the test. On the left side of the screen, a line feed shows where the camera is aimed, permitting the operator to position the patient in the correct location for optimal video capture. On the right side of the screen, a drop-down menu allows the operator to select a particular sound to be played from the speakers during the procedure. The intensity of the target LEDs can be controlled, as well as the image contrast. These options can allow the device to appeal to a wider audience, make the patient more comfortable, and increase cooperation and successful video capture.

Figure 14:
FIG. 14 is a screenshot of the user interface permitting review of the captured video prior to analysis.

After the video has been captured, FIG. 14 shows the next screen. Here, the video can be reviewed so that the operator can confirm that the video captured the appropriate information. For example, the operator may wish to capture a new video if the background lighting unexpectedly changed, or if the patient left the view of the camera.

Figure 15:
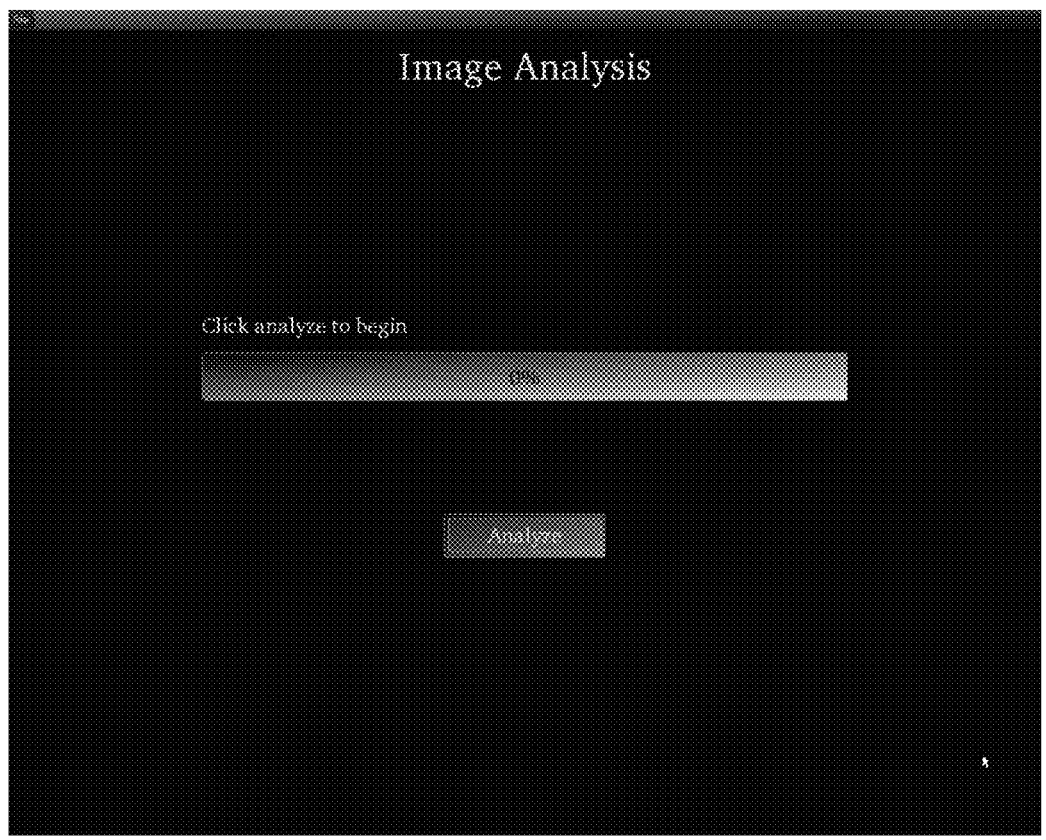
FIG. 15 is a screenshot of the user interface showing the real-time status of the analysis.

FIG. 15 shows the progress of the software analysis. Although not shown here, there may also be a visual confirmation of the contour fitting during the analysis to increase confidence in, and decrease error, in the software.

Two different reimbursement strategies are considered for use with the strabismus screening device of the present disclosure. The first reimbursement strategy is a pay-per-use strategy intended for simple screening. This strategy would provide users who have limited finances with a low initial investment opportunity for access to the device, such as schools and pediatric offices. The second reimbursement strategy is a full upfront pay strategy, which is intended for users that perform many strabismus corrective surgeries and would need the full capabilities, such as hospitals. It is contemplated that by using the present device, the number of corrective surgeries could be reduced, which would reduce overall costs as well.

Certain variations on the apparatus for diagnosing strabismus as described above are contemplated. Initially, the apparatus described in FIGS. 1-3 has three targets. However, it is contemplated that a similar apparatus could be used that has only two targets, or in other words only the zero target and a secondary target. The video camera and the light source would still be mounted above the zero target. It is also contemplated that the speakers are optional, though usually desirable.

Figure 16:
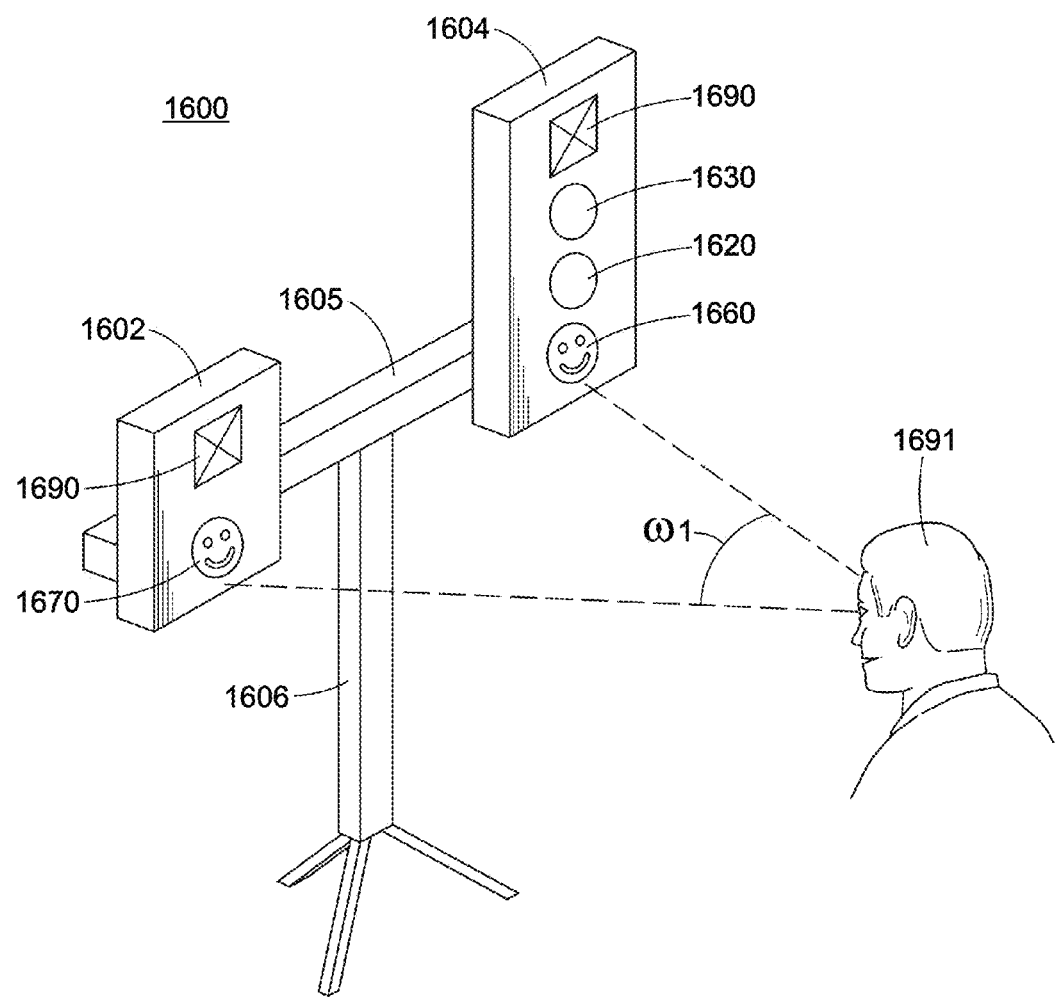
FIG. 16 is a perspective view of a second exemplary embodiment of an apparatus for diagnosing strabismus of the present disclosure. Here, the apparatus is in the form of two separate modules mounted on a transverse beam.
Figure 17:
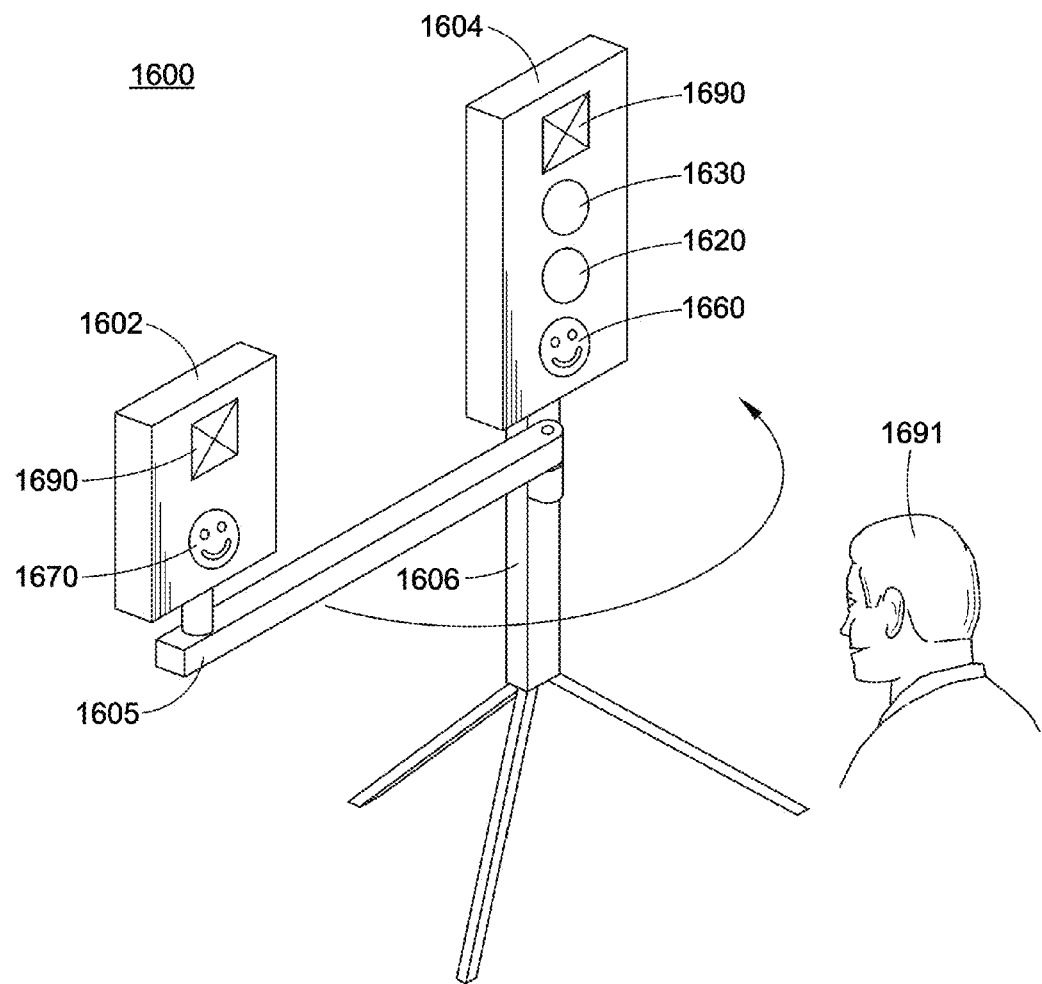
FIG. 17 is a perspective view of a third exemplary embodiment of an apparatus for diagnosing strabismus of the present disclosure. Here, the primary module is mounted on a vertical stand and the other module is mounted on a transverse beam. The transverse beam can be rotated so that the other module can be placed on either side of the primary module.
Figure 18:
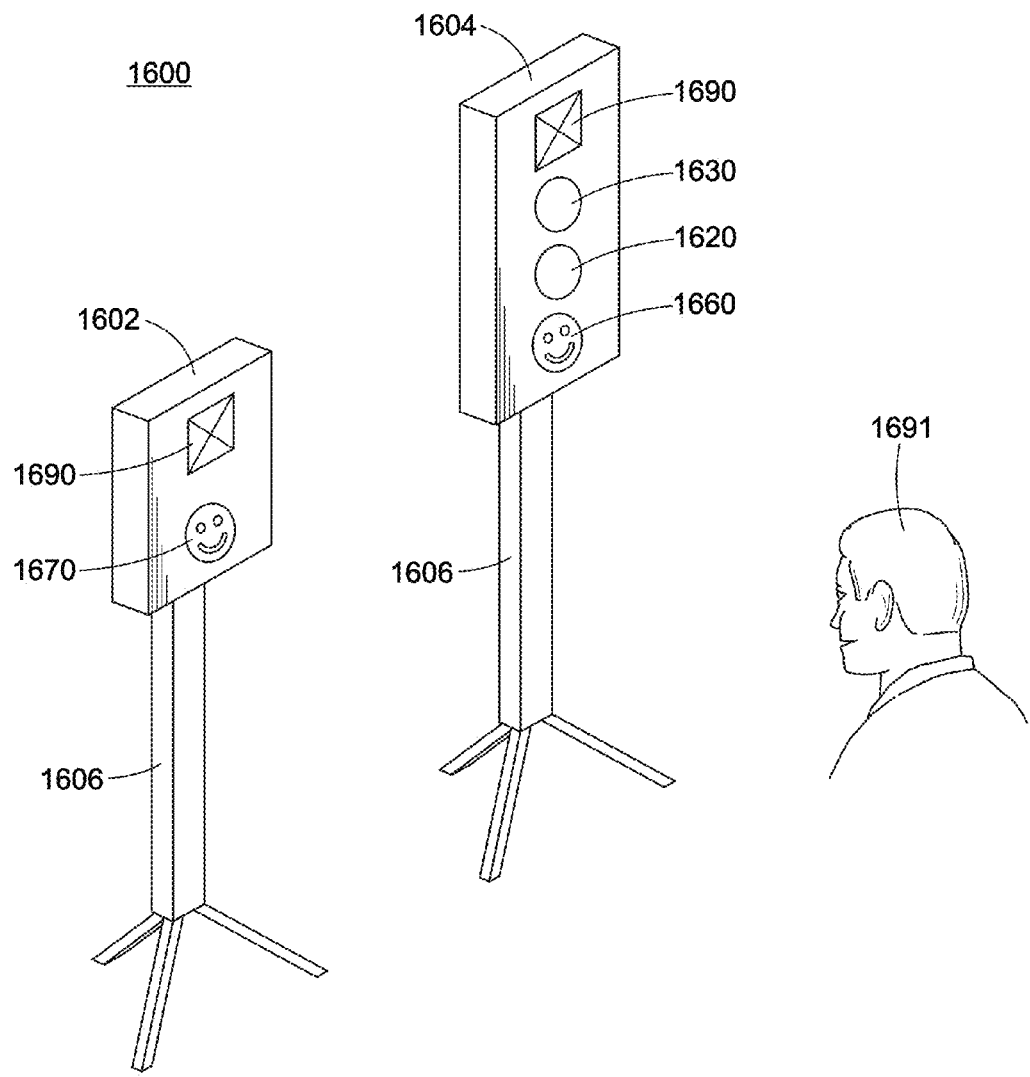
FIG. 18 is a perspective view of a fourth exemplary embodiment of an apparatus for diagnosing strabismus of the present disclosure. Here, the apparatus is in the form of two separate modules mounted on separate stands.

In other variations such as those depicted in FIG. 16 and FIG. 17 and FIG. 18, the apparatus 1600 is in the form of two physical modules 1602, 1604. One module 1602 contains a single target 1670 and the optional speaker 1690. The other module 1604 contains a single target 1660, a speaker 1690, the video camera 1620, and the light source 1630 for generating the Purkinje reflex, as well as the metering system if present (not depicted). This module 1604 (having the video camera 1620) is considered as containing the zero target. The modules may be snapped onto a transverse beam 1605 which is supported by a stand 1606. The snapping location is depicted here as being on the rear surface 1612 of the module, but could also be on the lower surface 1614.

In another embodiment depicted in FIG. 17, the primary module 1604 is mounted upon the vertical stand 1606. The transverse beam 1605 extends transversely from the vertical stand. The secondary module 1602 is mounted to the transverse beam. The transverse beam 1605 can be rotated around the stand (indicated by the arrow with the 180° arc), so that the secondary module 1602 can be on either side of the zero target.

Alternatively, as depicted in FIG. 18, the modules 1602, 1604 can be mounted on two separate stands 1606. In this regard, the software analysis relies on knowing the relative angle ω1 between the patient's head 1691 and the two modules 1602, 1604. This angle can be determined without needing to fix the two targets in place relative to each other. The computer for analyzing the video data is not illustrated in these two figures, but is still present. The heights of the two stands are individually adjustable. A third module is contemplated for embodiments where the apparatus has three targets.

Figure 19:
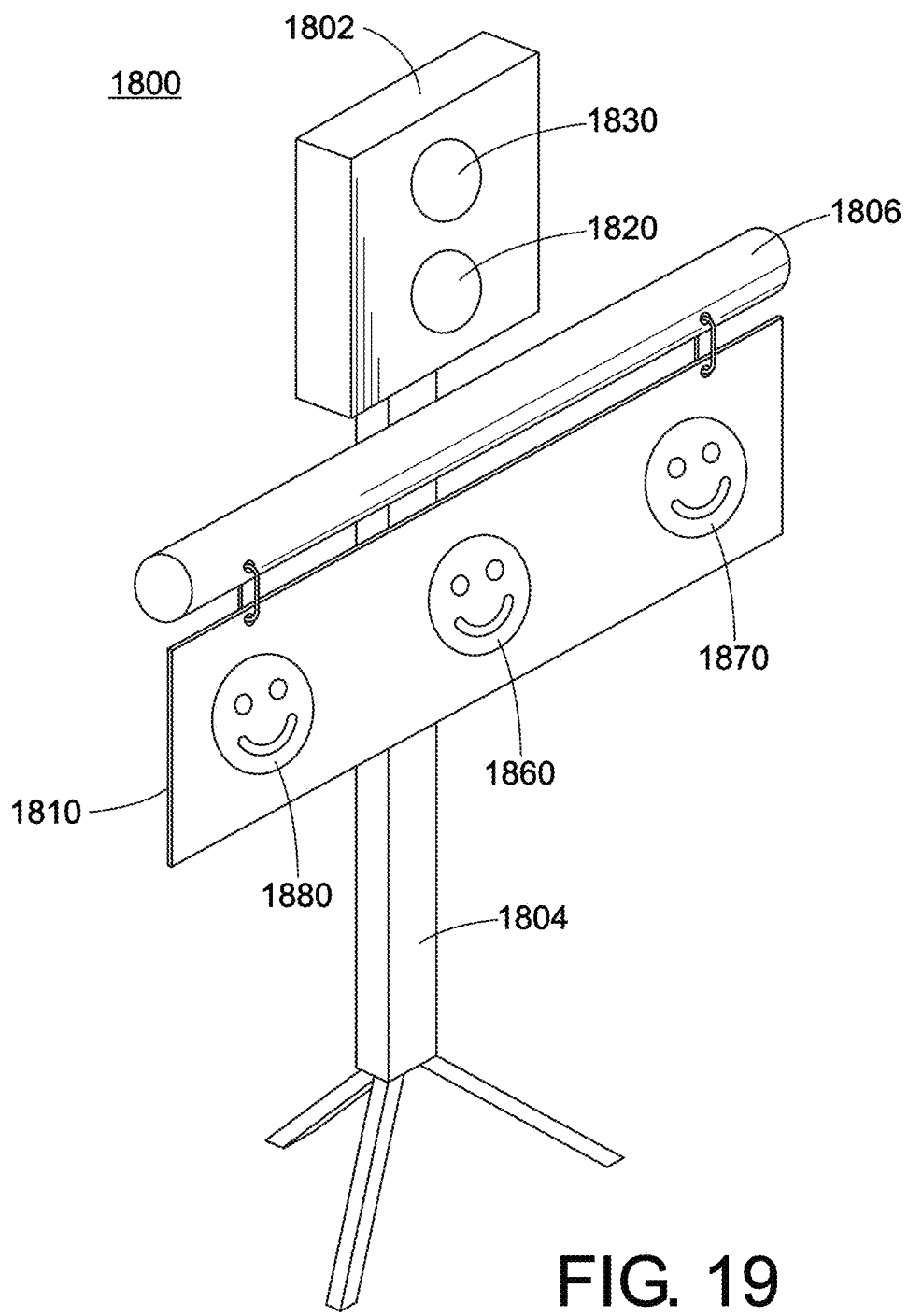
FIG. 19 is a perspective view of a fifth exemplary embodiment of an apparatus for diagnosing strabismus of the present disclosure. Here, the apparatus is in the form of a module having a flexible surface upon which the targets are mounted.

In another embodiment depicted in FIG. 19, the targets 1860, 1870, 1880 are mounted onto a flexible surface 1810, i.e. a material that can be bent or rolled up to minimize the size of the apparatus 1800 for easier transportation. As shown here, a vertical stand 1804 is used to support a module 1802 containing the video camera 1820 and the light source 1830 for generating the Purkinje reflex. The module can also contain the metering system if present. A crossbar 1806 extends transversely from the rigid stand 1804. The flexible surface 1810 is supported by the crossbar, displaying the targets to the patient. As depicted here, the flexible surface hangs from the crossbar. The speakers are not shown here, but could be provided along the crossbar if desired. The crossbar is shown here in a "cross" configuration with the vertical stand, but could take other configurations, for example a "T" or "L" configuration. The length of the crossbar may be adjustable, for example for easier storage or carrying. Alternatively, the vertical stand and the crossbar are not needed. Rather, the flexible surface 1810 and the module 1802 can be mounted upon, for example, a wall, using fasteners such as hooks, adhesive tape, etc.

In some other embodiments, it is contemplated that the video camera and the infrared light source are located behind the zero target itself. Put another way, the video camera and the infrared light source are located along an axis between the zero target and the patient's eyes.

It should be noted that wiring and connections for and between the different targets, modules, video camera, light source, and the computer are not illustrated for convenience and ease of understanding. The components needed to make the apparatuses for diagnosing strabismus, as well as the methods of making, are known in the art.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for determining and quantifying the angle of strabismus in a patient, comprising:
    using a video camera and a light source to capture a series of frames containing the patient's eyes as the patient's head remains in a stationary position relative to the camera and the eyes gaze at a zero target and at least one additional target;
    locating the Purkinje reflex and the pupil of a given eye by:
        in each frame, identifying brightest points in the frame to designate potential Purkinje points for a given eye in the frame;
        defining clusters based on the potential Purkinje points from all of the frames, wherein each cluster includes a potential Purkinje point and the number of frames containing the potential Purkinje point, and designating the cluster with the highest number of frames as identifying the Purkinje reflex for the given eye;
        for each frame, based on the location of the Purkinje reflex for the given eye, identifying a region of interest in the frame for the given eye; and
        within the region of interest, identifying the pupil for the given eye;
    subsequently sorting the frames into at least four different groups corresponding to each eye and which target the eye was gazing; and
    calculating the angle of strabismus by using linear regression to determine the y-intercept of the group corresponding to the zero target for the given eye;
    calculating the Hirschberg ratio for each eye, wherein the Hirschberg ratio for a given eye is calculated by:
        identifying a known angle for each group of the given eye;
        calculating a displacement between a centroid of the Purkinje reflex and a centroid of the pupil for each group of the given eye;
        plotting the known angle versus the displacement for the three groups of the given eye; and
        using linear regression to determine the slope of a best-fit line for the plot, wherein the slope is the Hirschberg ratio for the given eye.

2. The method of claim 1, wherein the patient's head is not fixed in position relative to the video camera.

3. The method of claim 1, wherein two additional targets are used, the two additional targets being a left target and a right target, and wherein the left target and the right target are independently located at an angle of 15° to 45° to opposite sides of the zero target relative to the patient's head.

4. The method of claim 3, wherein the left target is located 30° to the left of the zero target relative to the patient's head, and wherein the right target is located 30° to the right of the zero target relative to the patient's head.

5. The method of claim 1, wherein the brightest points in the frame are identified by processing to remove noise, thresholding to locate possible bright points, and then applying a size filter and an eccentricity filter to identify the brightest points; and wherein the pupil is identified by using an edge detection method and thresholding to detect possible edges, applying a size filter and an eccentricity filter to identify potential pupil edges, and using a curve fitting algorithm to identify the pupil.

6. The method of claim 1, wherein the video camera is mounted proximate the zero target, and wherein the light source is fixed in place relative to the video camera.

7. The method of claim 6, wherein the zero target, the light source, and the video camera are centered on a first line perpendicular to a second line connecting the zero target and the at least one additional target.

8. The method of claim 1, wherein the zero target, the video camera, and the light source are contained in a first physical module; and the at least one additional target is contained in a second physical module.

9. The method of claim 1, wherein the zero target and the at least one additional target are mounted on a flexible surface;

wherein the video camera and the light source are contained in a physical module mounted on a vertical stand; and wherein the apparatus further comprises a vertical stand and a crossbar extending transversely from the vertical stand, the physical module being mounted on the vertical stand and the crossbar supporting the flexible surface.

* * * * *